(12) United States Patent
Mason et al.

(10) Patent No.: US 6,839,137 B2
(45) Date of Patent: Jan. 4, 2005

(54) ASPHALTENE AGGREGATION IN PETROLEUM OIL MIXTURES DETERMINED BY SMALL ANGLE LIGHT SCATTERING

(75) Inventors: Thomas G. Mason, Summit, NJ (US); James C. Sung, Flemington, NJ (US); Zhengdong Cheng, Quincy, MA (US); Eric B. Sirota, Flemington, NJ (US); Michael Siskin, Randolph, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/458,811

(22) Filed: Jun. 10, 2003

(65) Prior Publication Data
US 2004/0012782 A1 Jan. 22, 2004

Related U.S. Application Data
(60) Provisional application No. 60/397,002, filed on Jul. 19, 2002.

(51) Int. Cl.⁷ .......................... G01N 21/00; G01N 33/28
(52) U.S. Cl. ......................................... 356/338; 356/70
(58) Field of Search ................................ 356/335–343, 356/70, 73, 128; 208/177, 208 R, 251 R, 48 R; 250/339.09, 339.12, 226; 585/1, 950

(56) References Cited

U.S. PATENT DOCUMENTS

| | | | | |
|---|---|---|---|---|
| 4,843,247 A | * | 6/1989 | Yamazoe et al. | 250/573 |
| 5,719,665 A | * | 2/1998 | Yamazoe | 356/70 |
| 5,871,634 A | * | 2/1999 | Wiehe et al. | 208/48 R |
| 5,997,723 A | * | 12/1999 | Wiehe et al. | 208/48 R |
| 6,087,662 A | * | 7/2000 | Wilt et al. | 250/339.12 |
| 6,501,072 B2 | * | 12/2002 | Mullins et al. | 250/256 |
| 6,549,276 B1 | * | 4/2003 | Longtin | 356/128 |

* cited by examiner

*Primary Examiner*—Hoa Q. Pham
(74) *Attorney, Agent, or Firm*—Ronald D. Hantman

(57) ABSTRACT

The present invention includes a method to determine if asphaltenes are soluble or insoluble in a solution. The solution may be a petroleum oil, a mixture of petroleum oils, petroleum derived oils and mixtures or similar combinations in a solvent. The invention includes the steps of illuminating the solution with a laser, measuring the small angle scattered light as a function of angle away from the laser beam, and determining if the asphaltenes are soluble or insoluble in the solution.

11 Claims, 5 Drawing Sheets

ASPHALTENE AGGREGATION IN PETROLEUM OIL MIXTURES DETERMINED BY SMALL ANGLE LIGHT SCATTERING

This application is a Non-Provisional of Provisional U.S. Ser. No. 60/397,002 filed Jul. 19, 2002.

BACKGROUND OF THE INVENTION

The present invention relates to the aggregation of asphaltenes. In particular, the present invention includes a method to determine aggregation and steps to avoid the aggregation of asphaltenes when blending petroleum oils.

Asphaltenes are a solubility class fraction of a petroleum oil or refinery process stream that typically aggregate or precipitate out of solution when concentrated, the temperature is changed, and/or when a nonpolar solvent, petroleum oil, or process stream is mixed or blended with it. Asphaltenes represent a wide variety of hydrocarbon molecules that are typically polyaromatic in nature with some degree of alkyl substitution present and which usually contain heteroatoms such as oxygen, nitrogen, and sulfur and metal atoms in their structures. Asphaltenes are usually found in significant quantities in heavy crude oils and refinery residua, and they are believed to sometimes self-assemble into colloidal micelle-like structures of several molecules that remain suspended in solution due to their small size and the possible solvating effects of other types of molecules in the petroleum oil or process stream. These micelle-like structures of several molecules are sometimes referred to as "asphaltene particles" in order to differentiate them from the single "asphaltene molecules" that may also be present in solution or suspension in the oil. The asphaltene particles are typically smaller than twenty nanometers in size, but this can vary depending upon the source of the petroleum oil or process stream and their concentration in the oil.

It is well known that insoluble asphaltenes may precipitate when two or more unprocessed petroleum crude oils and/or refinery process streams are blended together. The term "asphaltene aggregate" refers to the formation of larger precipitated clusters of asphaltene particles and molecules that stick together due to an attractive interaction that has been reinforced, when for example, the nonpolar petroleum oil and/or refinery process stream is blended into the oil containing the asphaltenes. These asphaltene aggregates are typically a micron in size and are sometimes large enough to be observed with the unaided naked eye. These aggregates are also typically physically and optically more dense than the surrounding oil mixture from which they precipitated, so they tend to slowly sediment. If the blending of such oils and/or process streams causes the aggregation or precipitation of asphaltenes, then the oils are said to be incompatible as opposed to compatible oils that do not precipitate asphaltenes on blending. Precipitated asphaltenes are not desirable, as they are known to foul and lead to fouling of process equipment when rapidly heated to high temperatures.

SUMMARY OF THE INVENTION

The present invention includes a method to determine if asphaltenes are soluble or insoluble in a solution. The solution may be a petroleum oil, a mixture of petroleum oils or a petroleum oil in a solvent. The invention includes the steps of illuminating the solution with a laser, measuring the scattered light as a function of angle away from the laser beam at small angles, and determining if the asphaltenes are soluble or insoluble in the solution.

The invention also includes a method to determine the insolubility number, $I_N$, and the solubility blending number, $S_{BN}$, of a petroleum oil, mixtures of different petroleum oils and petroleum derived oils using small angle light scattering (SALS) to detect asphaltene aggregation that may occur in such mixtures. Asphaltene aggregates present in such mixtures have been linked to the fouling of refinery process equipment, such as heat exchangers and furnaces through the buildup of coke on the pipe walls.

A method for predicting the compatibility of crude oils has been disclosed in patents, U.S. Pat. No. 5,997,723 and U.S. Pat. No. 5,871,634, incorporated herein by reference, and this method relies upon empirically determined values of $I_N$ and $S_{BN}$ for the individual petroleum oils. In the present invention, angle-dependent SALS of petroleum oil, petroleum derived oils, and mixtures provide a more sensitive means of detecting the onset of asphaltene aggregation, and therefore is used to assess petroleum oil incompatibility. The SALS apparatus includes a laser beam illuminating the petroleum oil mixture contained within a thin, optically-clear cell and measuring the scattered light intensity as a function of the angle away from the laser beam using a light detector, such as a charged-coupled device (CCD) array. SALS can be used not only to determine $I_N$ and $S_{BN}$ for a crude oil by dilution with, e.g., mixtures of heptane and toluene, but it can also be used to refine the oil compatibility model by directly measuring the onset of asphaltene aggregation in mixtures of crude oils and petroleum derived oils. SALS can be used to measure the growth of aggregates and, because the full scattered light intensity as a function of angle is measured, structural information about the morphology of the aggregates can be obtained. Additionally, SALS can be used to detect the disaggregation of asphaltene aggregates present in incompatible crude oil mixtures if such mixtures are heated, or otherwise treated or the precipitation of asphaltene aggregates when cooled. For maximum sensitivity, the measurements are best performed with departiculated crude oils (e.g. free of wax or coke particles), achieved for instance by centrifugation, heating or filtration, but they can also be performed with oils containing solid particulates, albeit with reduced sensitivity to the asphaltene aggregation.

DETAILED DESCRIPTION OF THE PREFERRED EMBODIMENTS

The invention uses a small angle light scattering apparatus to measure the laser light scattered at small angles by asphaltene aggregates which may be present in a petroleum oil, petroleum oil mixture, petroleum derived oils and mixtures in order to determine the range of mixing ratios over which incompatibility (i.e. asphaltene aggregation and precipitation) occurs. By examining a large number of mixing ratios and varying the aliphatic/aromatic solvent quality, it is now possible to determine the onset of asphaltene aggregation precisely, and thereby deduce $I_N$ and $S_{BN}$ and improve the predictions of oil compatibility. Alternatively, by directly examining a mixture of crude oils, as described below, one may directly assess the range of mixing incompatibility and even the kinetics of the asphaltene aggregate growth and/or disaggregation.

Figure 1:
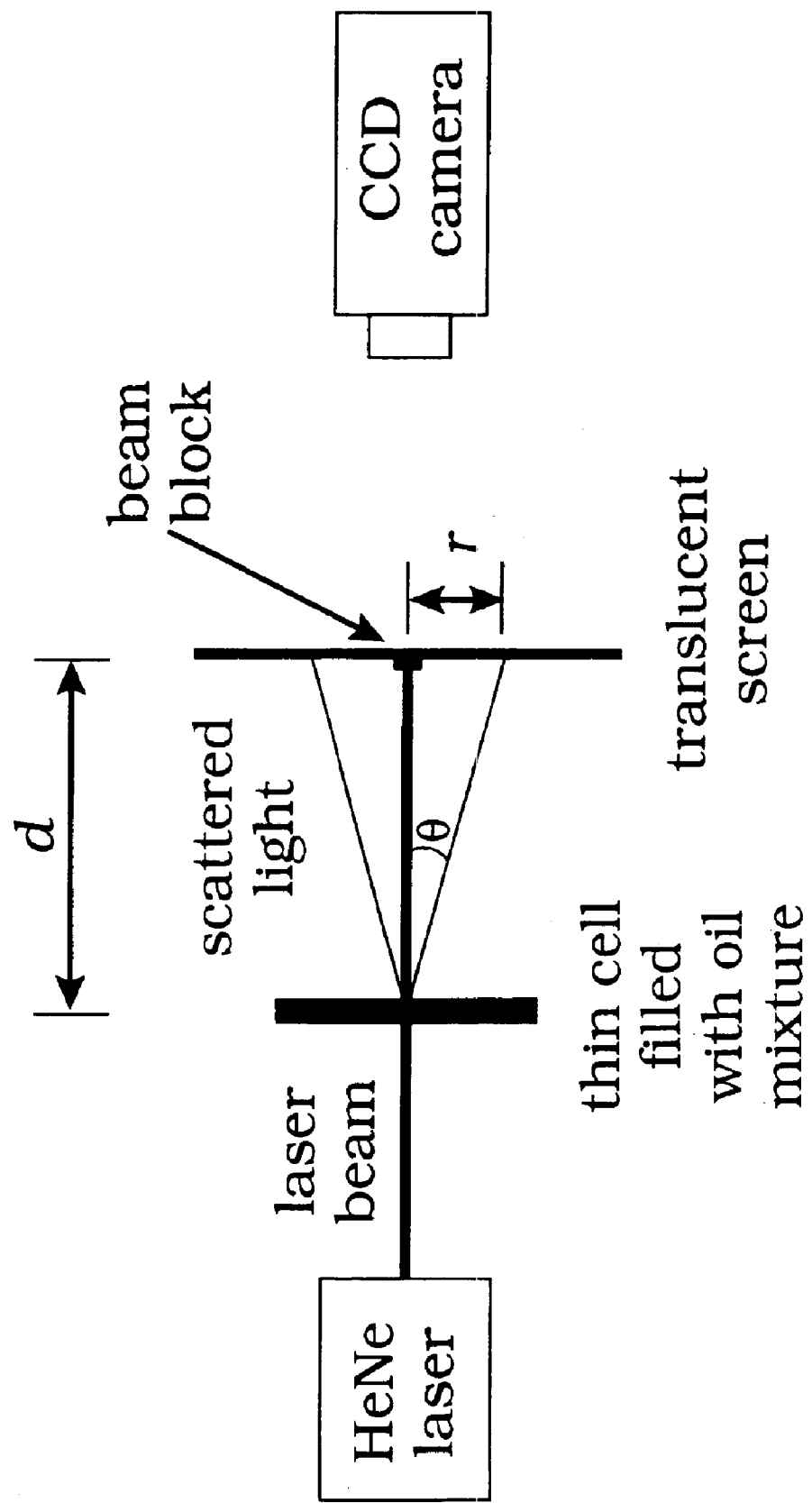
FIG. 1 shows a schematic diagram of the SALS apparatus. Red laser light is scattered by asphaltene aggregates in the cell and the scattered light forms a speckle pattern on the screen. This speckle pattern is imaged by a CCD camera and acquired by a frame-grabber card on a computer. A customized version of the public domain NIH Image software calculates the azimuthally-averaged intensity as a function of wavenumber, I(q), using the cell-screen distance d, for various distances of scattered light away from the beam's center, r.

As shown schematically in FIG. 1, one embodiment of the SALS apparatus consists of a monochromatic helium-neon laser beam at a wavelength of λ=632.8 nm and a power of 5 mW that illuminates a flat quartz cell holding a complex fluid, and the light scattered by structures within the fluid falls on a translucent screen positioned a distance, d, beyond the cell. A thick black circular beam stop glued to the screen blocks the transmitted beam, and an 8-bit monochrome CCD camera (720×480 pixels) equipped with a lens is focused on the screen to image the scattered light intensity. The CCD camera, which has been verified to provide a linear response proportional to the light intensity, is connected to a computer-controlled frame grabber that captures these images. Other light detectors or digital cameras could be used; the one described here is an example. Because the laser light is coherent, the scattered light typically forms a speckle pattern on the screen. For isotropic complex fluids, the speckle-filled scattering pattern is typically symmetric about the beam stop; by taking an azimuthal average of the intensity in an annular region, one is able to smooth out the intensity fluctuations introduced by the speckles. By moving the cell exposed to the beam while averaging the intensity over 30 CCD frames, it is possible to obtain a better ensemble average of the scatterers and further reduce the variations in intensity due to speckles by effectively spatially averaging over many aggregates. The intensity, I, that we report is always this azimuthally-and spatially-averaged quantity. By calibrating the distance from the center of the beam on the screen, r, the scattering angle is defined as θ=tan⁻¹(r/d). From this angle, we obtain the scattering wavenumber, q:

$$q=(4\pi n/\lambda)\sin(\theta/2), \tag{1}$$

where n is the refractive index of the liquid (i.e. oil). Using a refractometer, the refractive index of the Forties oil is n=1.470±0.005 (we neglect the small change that different amounts of Souedie oil could make). The range of q values which the apparatus probes can be changed by varying the distance between the cell and the screen and also by changing the type of lens on the CCD camera to alter the effective field of view. In this set of experiments, we do not change either the lens, the distance, or the laser intensity; thus, although the resulting intensity is expressed in arbitrary units, we can nevertheless quantitatively compare intensities measured for different samples. The lowest q is ultimately limited by the radius of the black beam stop that prevents the very bright-transmitted laser beam from appearing on the screen. Finally, the background scattering from imperfections or residue initially on the cells is subtracted from the reported intensities.

Because solid wax crystals and other particulates that are sometimes present in crude oils scatter light significantly, it is desirable to eliminate them from the crude oils before blending to probe asphaltene aggregation. We dewaxed the Souedie and Forties crude oils using mild centrifugation at about 2,500 revolutions per minute at room temperature. This dewaxing procedure reduces the initial background scattering and provides a better differentiation of the scattering intensity associated with asphaltene aggregates. Alternatively, the measurement may be run at higher temperatures. However, unless the contamination of the oil by solid wax, other particulates, or even emulsion droplets and air bubbles is extreme, it is possible to avoid this step, realizing that one would then be looking for a change in the scattered light intensity relative to a significant background value due to these non-asphaltene aggregate scatterers.

Figure 2:
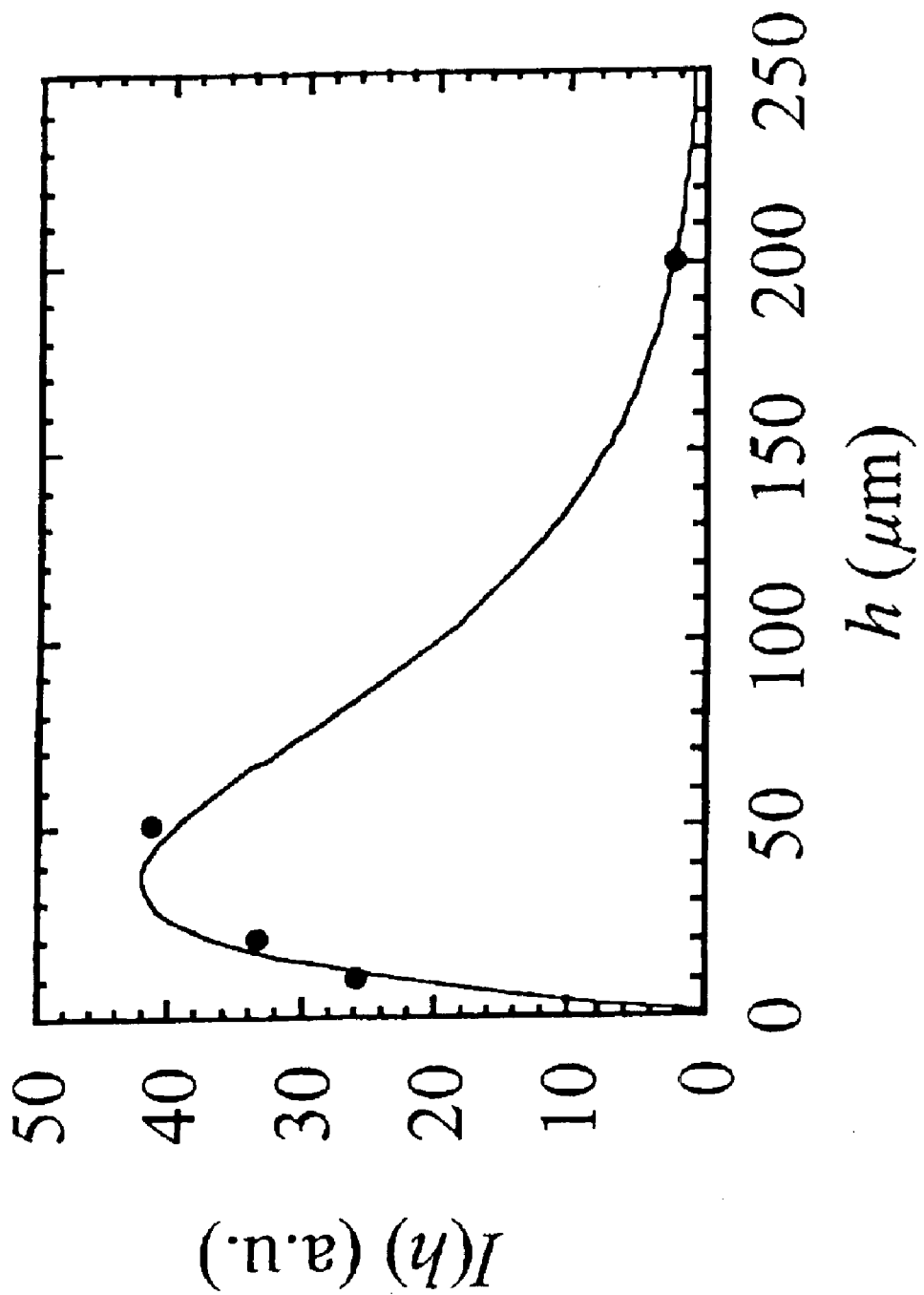
FIG. 2 shows the measured SALS intensity, I, as a function of cell thickness, h, for a mixture of Souedie+Forties oil ($\phi_m=0.3$) at a fixed wavenumber $q=0.1\ \mu m^{-1}$. The line is a fit to the equation having a linear rise at low h due to the increasing cell thickness with an exponential cutoff at high h due to optical absorption. The characteristic extinction length due to absorption from the fit is $l_e=36\pm 8\ \mu m$.

Before investigating the temporal evolution of the scattering from recently mixed samples of dewaxed Souedie and Forties, we first varied the cell thickness to optimize (i.e. maximize) the observed scattering from an incompatible mixture at $\phi_m$=0.3 that had been made many months before and contained many large asphaltene aggregates. Here, $\phi_m$ is defined to be the mixing volume fraction of the heavy oil (Souedie) in the light oil (Forties). In FIG. 2, we plot the low-q scattering intensity (where the scattering is the strongest) as a function of the cell thickness, h. We clearly observe a maximum in I(h) around h≈50 μm, which is comparable to the optical extinction length, $l_e$, of the crude oil mixture. We reason that this maximum exists based on two limiting cases: (1) at the smallest cell thicknesses there are fewer aggregates in the beam, so the intensity vanishes as h→∞. A fit of the data to a form I(h)~h exp(−h/$l_e$) yields an extinction length is shown as the solid line in FIG. 2, and $l_e$=36±8 μm from the fit. Because the stronger optical absorption by the heavy Souedie oil might make observations in a thicker cell more difficult at larger $\phi_m$, we use the h=50 μm cell in our measurements. All of our measurements have been carried out at room temperature, T=23° C., except for those in which we specifically mention temperature control.

Figure 3:
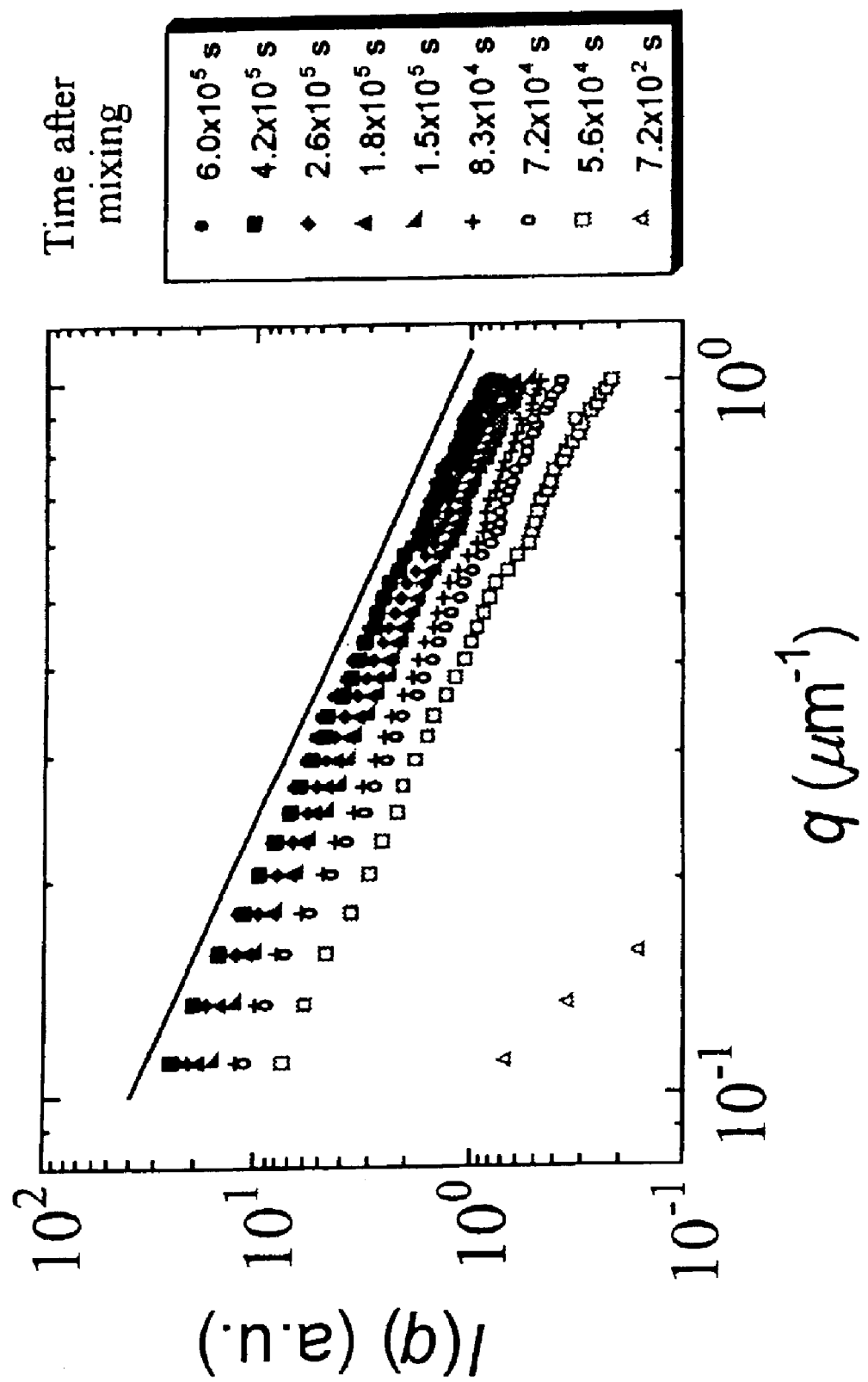
FIG. 3 shows the SALS intensity, I, as a function of wavenumber q, for Souedie/Forties mixtures at a mixing volume fraction of $\phi_m=0.33$ for a series of times after mixing and immediately loading into the 50 $\mu m$ cell (symbols and times are defined by the legend). The solid black line, which characterizes the power law decrease of I(q), has a slope of −1.5 on this log-log plot.

Our first set of SALS measurements have been made by mixing the dewaxed crude oils together, immediately loading them in the cell, sealing the cell, and placing the cell containing the incompatible mixture in the SALS apparatus. Since no shear is applied to the cell after sealing it, the motion of the asphaltenes is presumably diffusive. The measured I(q) for a series of times, t, are shown in FIG. 3 for $\phi_m=0.33$. In this plot, the scattering is negligible at early times right after mixing, and it increases more rapidly at low than at high q, and, at long times (after about a day) I(q) ceases to change significantly. At long times, I(q) for $\phi_m=0.33$ exhibits a power law behavior with an exponent of −1.5, as shown by the solid black line in FIG. 3.

Figure 4:
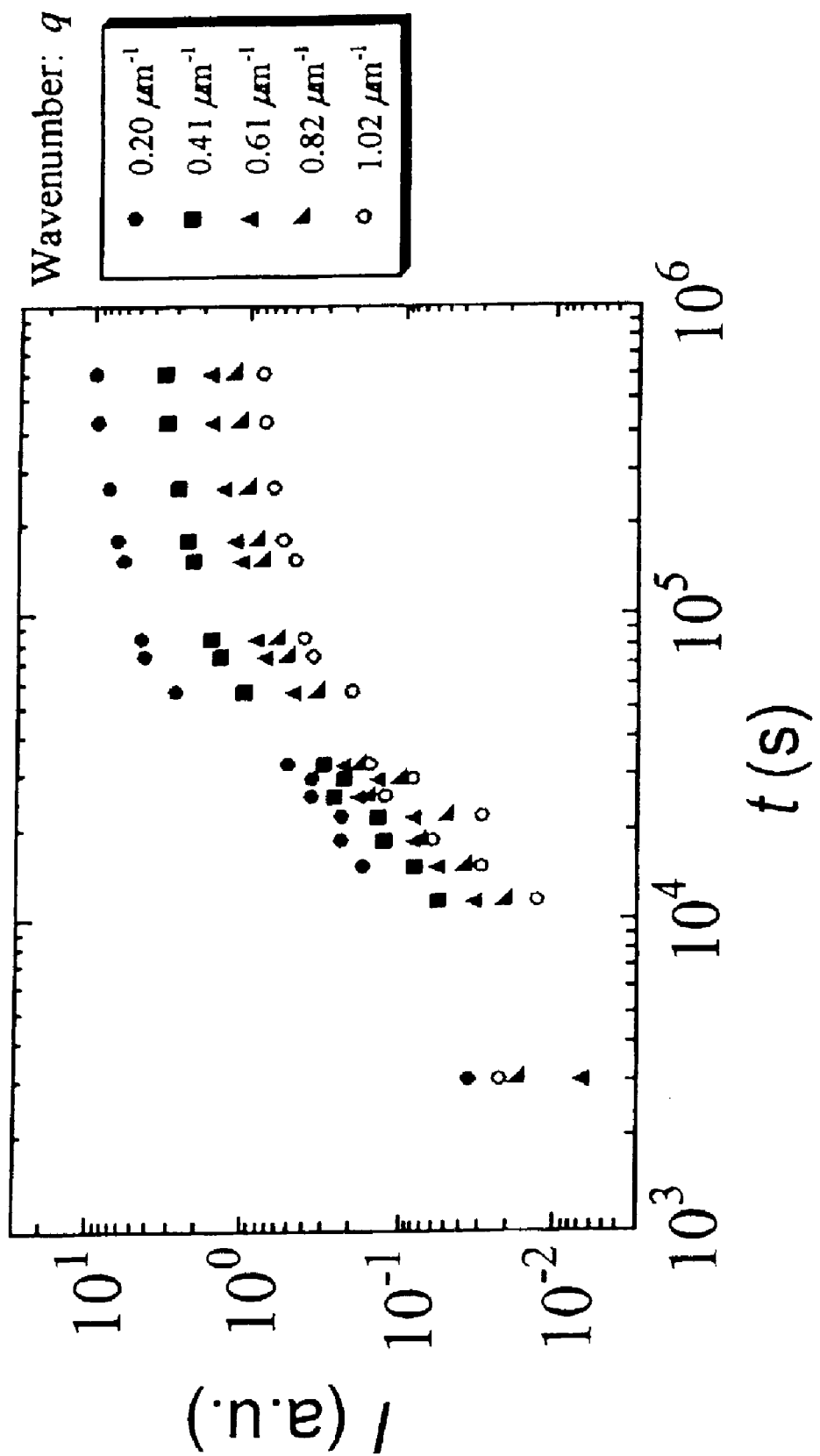
FIG. 4 shows the SALS intensity, I, as a function of time, t, for Souedie/Forties mixtures at a mixing volume fraction of $\phi_m$=0.33 for a series of wavenumbers, q, after mixing and immediately loading into the 50 μm cell (symbols and wavenumbers are defined by the legend). At all q, the SALS intensity grows initially more slowly than in FIG. 4 and saturates at longer times.

To show the temporal dependence of the initial increase and subsequent saturation of the scattered intensity more clearly, the data in FIG. 3 are replotted as a function of time in log-log format for several selected q values in FIG. 4. The initial rise and final saturation of the intensity are clearly observed at all q probed. This shows that, in a sealed cell without mechanical agitation, the time scale for the cessation of diffusion-driven aggregation can be several days. It also demonstrates the capability of the instrument for measuring the time-dependence of aggregation or disaggregation after a change in the solvent quality from aromatic to aliphatic.

Figure 5:
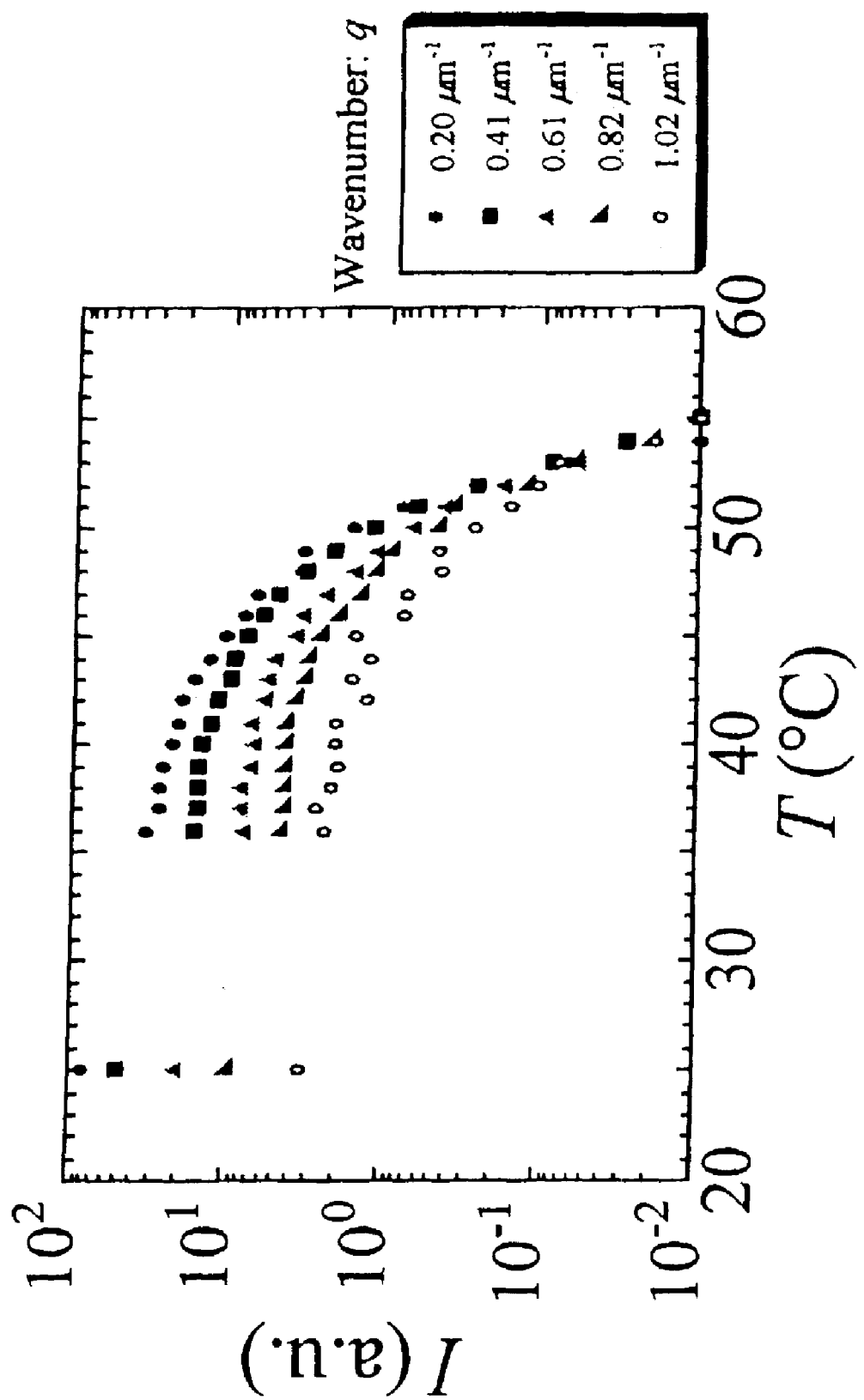
FIG. 5 shows the SALS intensity, I, as a function of temperature, T, for asphaltenes from Cold Lake bitumen dispersed at 3% by mass in a model liquid solvent of 64:36 ratio of dodecane: 1-methylnaphthalene. The mixture has been heated to T≈100° C. and the asphaltenes are dispersed. The temperature is then lowered in a continuous ramp down toward room temperature at a rate of about 1° C./min. As the mixture cools, the asphaltenes aggregate and we measured the increase in the scattered light intensity at different wavenumbers. The temperature corresponding to the onset of aggregation can be defined to be T*=54° C.

Finally, we show that, by equipping the apparatus in FIG. 1 with a thermal stage to control the cell temperature, we are able to measure the onset of asphaltene aggregation induced by temperature changes as a function of wavenumber. In this case, the sample consists of 3% by mass of Cold Lake bitumen asphaltenes dispersed in an ideal liquid solvent of dodecane: 1-methylnaphthalene at a mass ratio of 64:36. This solvent mixture has been chosen to reduce the pressurization of the cell that would occur with lighter solvents such as heptane and toluene, and this particular solvent mass ratio has been chosen to be close to the asphaltene aggregation point at room temperature, but nevertheless does cause aggregates to form at room temperature. This mixture containing the aggregates is then heated to T≈100° C., the asphaltenes aggregates present at room temperature redisperse, and the SALS intensity vanishes. The temperature is then lowered in a continuous ramp down toward room temperature at a rate of about 1° C./min. As the mixture cools, the asphaltenes aggregate and we measured the increase in the scattered light intensity over several orders of magnitude at different wavenumbers. Thus, using SALS, we can define the temperature corresponding to the onset of asphaltene aggregation to be T*≈54° C. These results for using SALS to characterize the asphaltene aggregation and disaggregation behavior due to temperature changes are shown in FIG. 5.

EXAMPLE

Determining $I_N$ and $S_{BN}$ for a Crude Oil Using SALS

The compatibility parameters $I_N$ and $S_{BN}$ for a petroleum oil are obtained by the following procedure which essentially replaces the microscopic method for detecting asphaltene aggregates (see U.S. Pat. No. 5,997,723 and U.S. Pat. No. 5,871,634) with the present invention, the SALS method for detecting asphaltene aggregates. A volume $V_{oil}$ the departiculated petroleum oil (e.g. Souedie) is diluted with an aromatic solvent (e.g. toluene) of volume $V_{aro}$. A volume $V_{ali}$ of a non-polar aliphatic solvent (e.g. n-heptane) is added to this mixture and stirred. Any possible asphaltene aggregation is allowed to proceed as in U.S. Pat. No. 5,997,723 and U.S. Pat. No. 5,871,634. The thin optical cell is loaded with the mixture, and I(q) is measured using the SALS apparatus. For fixed $V_{oil}$ and $V_{aro}$, by repeating the SALS measurement for different $V_{ali}$, a set of SALS intensities I(q, $V_{ali}$) are obtained. A wavenumber q* (typically 0.3 $\mu m^{-1}$) is fixed and I($V_{ali}$) at q=q* is plotted. For low $V_{ali}$, there is very little scattering corresponding to no aggregation; however, for larger $V_{ali}$, when $V_{ali}$ exceeds a certain value V*, then the scattered light intensity grows rapidly above the background level. Typically, V* is defined as the $V_{ali}$ above which the scattered light intensity increases by at least a factor of two over the average background level. The three volumes, $V_{oil}$, $V_{aro}$, and V*, then define one point on the incompatibility phase boundary for that crude oil and choice of aromatic and aliphatic solvents. Additional points on the incompatibility phase boundary can be obtained by varying the oil volume and/or the aromatic solvent volume and repeating the measurement of I(q, $V_{ali}$) to give different values of V*. With three or more sets of volumes ($V_{oil}$, $V_{aro}$, V*), the best $I_N$ and $S_{BN}$ are calculated by performing a least squares fit of all points on the plot described in U.S. Pat. No. 5,997,723 and U.S. Pat. No. 5,871,634. Two sets of volumes are sufficient to give a straight line, but the precision of the measurement of $I_N$ and $S_{BN}$ improves as more sets of volumes are measured and included in the fit.

This procedure can be applied with a petroleum oil or petroleum oil mixture that has not been departiculated, albeit with reduced sensitivity to the presence of asphaltene aggregates.

Restated, the invention includes a method for using small light scattering to probe petroleum oil mixtures for asphaltene aggregates. In many cases, it is advantageous to keep the cell thickness small so as to reduce the effects of optical absorption and multiple scattering. We have shown how to determine an optimal cell thickness. One could also pressurize the system to detect how pressure affects the concentration and morphology of asphaltene aggregates. Alternatively, one may use laser illumination at a different wavelength than the one we have chosen for red light (e.g. there may be less light absorption in the infrared region at higher wavelengths), but the underlying principle of operation is the same.

What is claimed is:

1. A method to determine if asphaltenes are soluble or insoluble in a solution comprising:

(a) illuminating said solution with a laser beam, (b) measuring scattered light intensity as a function of angle away from the laser beam, (c) determining if asphaltenes are soluble or insoluble in said solution by the increase in scattered light intensity with the onset of asphaltene aggregation.

2. The method of claim 1 wherein said solution includes one or more petroleum oils.

3. The method of claim 1 wherein said solution includes petroleum oil and aromatics liquids and aliphatic liquids.

4. The method of claim 3 wherein said solution includes one or more petroleum oils and toluene or heptane.

5. The method for claim 3 further comprising the steps of measuring the insolubility number and the solubility blending number for petroleum oil.

6. The method of claim 4 wherein said insolubility number and said solubility blending number are determined from the toluene equivalence test and the heptane dilution test for each petroleum oil containing asphaltenes.

7. The method of claim 2 further comprising the step of determining the onset of asphaltene aggregation in said solution.

8. The method of claim 2 further comprising the step determining the onset of asphaltene disaggregation in said solution.

9. The method of claim 2 further comprising the step of maintaining said solution at a predetermined temperature.

10. The method of claim 9 wherein said predetermined temperature is determined by an increase in the measured intensity above the intensity that has been measured at high temperature when no aggregates are present.

11. The method of claim 10 wherein said predetermined temperature is about 54° C.

* * * * *